ns Patent Number: 5,019,642
Date of Patent: May 28, 1991

[54] NOVEL DIAMINE COMPOUNDS, PRODUCTION OF THE SAME AND POLYAMIDEIMIDE RESINS PRODUCED THEREFROM

[75] Inventor: Takeshi Hashimoto, Shizuoka, Japan

[73] Assignee: Tomoegawa Paper Co., Ltd., Tokyo, Japan

[21] Appl. No.: 491,988

[22] Filed: Mar. 12, 1990

[30] Foreign Application Priority Data

Mar. 10, 1989 [JP] Japan .................................. 1-56192
Apr. 13, 1989 [JP] Japan .................................. 1-91892
May 12, 1989 [JP] Japan .................................. 1-117556
Jun. 30, 1989 [JP] Japan .................................. 1-166580

[51] Int. Cl.$^5$ ...................... C08G 73/14; C08G 65/38; C08G 69/26; C07C 255/00
[52] U.S. Cl. .................................. 528/353; 528/170; 528/212; 558/413
[58] Field of Search ................ 558/413; 528/170, 212, 528/353

[56] References Cited

U.S. PATENT DOCUMENTS 3,382,261  5/1968  Kittredge et al. .................. 528/212

OTHER PUBLICATIONS

Patent Abstracts of Japan, unexamined application, C field, vol. 10, No. 310, Oct. 22, 1986, p. 155 C 379 Kokai-no. 61-122 255.
Patent Abstracts of Japan, unexamined applications, C field, vol. 9, No. 241, Sep. 27, 1985, p. 50 C 306, Kokai-no. 60-99 133.

Primary Examiner—John Kight, III
Assistant Examiner—Kathryne J. Shelborne
Attorney, Agent, or Firm—Oblon, Spivak, McClelland, Maier & Neustadt

[57] ABSTRACT

A diamine compound represented by general formula (I):

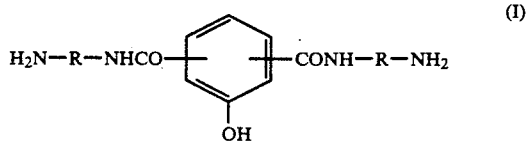

wherein R is as defined in the specification a group of formula (II)

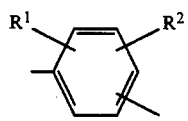

where $R^1$ and $R^2$ as defined in the specification or a group of formula (III)

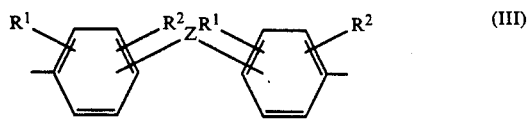

where $R^1$ and $R^2$ have the same meanings as defined above, and Z is as defined in the specification, or —$SO_2$—. The diamine compound is produced by reducing a dinitro compound of general formula (IV)

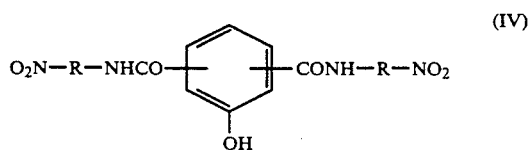

wherein R has the same meaning as defined above. Imidation of the diamine compound with a tetracarboxylic acid dianhydride produces a polyamideimide resin having a repeating unit represented by general formula (V):

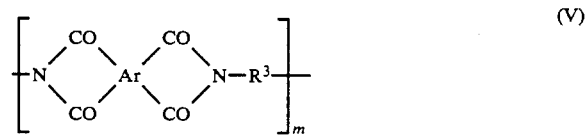

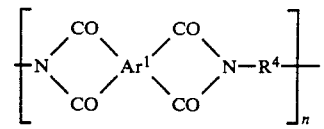

wherein Ar and $Ar^1$, which are as defined in the specification $R^3$ is a group of general formula (VI) below:

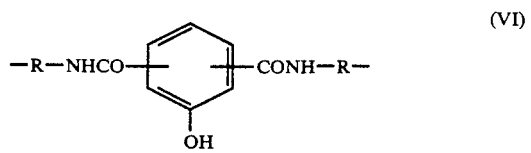

where R has the same meaning as defined above; $R^4$ is as defined in the specification and m and n are each zero or a positive integer which satisfy $m \geq 2n$.

3 Claims, No Drawings

NOVEL DIAMINE COMPOUNDS, PRODUCTION OF THE SAME AND POLYAMIDEIMIDE RESINS PRODUCED THEREFROM

BACKGROUND OF THE INVENTION

1. Field of the Invention

The present invention relates to novel diamine compounds, particularly those which are useful as a monomer for producing high polymers, and a method of producing the diamine compounds. It also relates to novel polyamideimide resins produced from the diamine compounds.

2. Description of Related Arts

Polyimide resins and polyamide resins have been used widely in various fields such as films, coverings of electric wires, adhesives, paints, laminates and the like making a good use of its excellent characteristics, in particular heat resistance. On the other hand, development of polyamideimide resins, polyester imide resins, polyether imide resins and the like have been under way in order to broaden the applicability of the polyimide resins and polyamide resins while maintaining their advantages.

However, polyimide resins, polyamide resins, polyamideimide resins and the like which are now used widely have poor molding characteristics although they have sufficient heat resistance. In order to keep the balance between the advantage and disadvantage of the resins, it has been studied to compound the base resins, i.e., polyimide resins, polyamide resins, polyamideimide resins and the like, with other reactive resins such as epoxy resins. However, this approach has been unsuccessful. Major problems are that the resulting resins are insoluble or slightly soluble in solvents due to poor solubility of the base resins, and that the base resins do not mix uniformly with the reactive resins in a desired proportion, with the result that no desired characteristics can be obtained by blending.

On the other hand, diamine compounds have been used as raw materials for producing polyimide resins, polyamide resins, polyamideimide resins and the like in order to give heat resistance thereto and also as a curing agent for epoxy reins and as intermediates for producing dyestuffs and the like. When aromatic diamines such as 4,4'-diaminodiphenyl ether and 4,4'-diaminodiphenylmethane are used to produce polyimide resins, polyamide resins, polyamideimide resins and the like, the resins obtained have poor molding characteristics although they have sufficient heat resistance as described above.

SUMMARY OF THE INVENTION

It is an object of the present invention to provide a diamine compound which is useful as a raw material for producing a polyimide resin, a polyamide reins, a polyamideimide resin and the like that have active sites for epoxy compounds and can be mixed with epoxy resins uniformly, thereby enabling compounding with epoxy resins.

It is another object of the present invention to provide a method of producing such diamine compound.

It is still another object of the present invention to provide a polyamideimide resin which is soluble in an organic solvent and which has active sites for other reactive resins, thus enabling compounding therewith.

As the result of intensive investigation, it has now been found that the use of diamine compounds having specified chemical structures meets the above-described objects.

Therefore, the present invention provides a diamine compound represented by general formula (I) below:

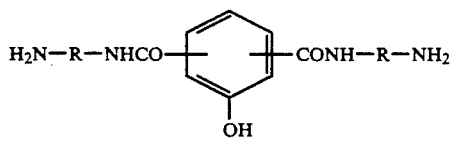

wherein R is a $C_1$-$C_{12}$ alkylene group which is unsubstituted or substituted, a group of formula (II) below

where $R^1$ and $R^2$, which are the same or different, each represents a hydrogen atom, a lower alkyl group, a halogen atom, a nitrile group, a nitro group, an alkoxy group or a hydroxyl group, or a group of formula (II))

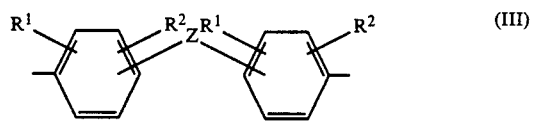

where $R^1$ and $R^2$ have the same meanings as defined above; and

Z is a simple chemical bond, —O—, >C=O, —CH$_2$—, —S—, —SO—, or —SO$_2$—.

In another aspect, the present invention provides a method of producing a diamine compound represented by general formula (I) below:

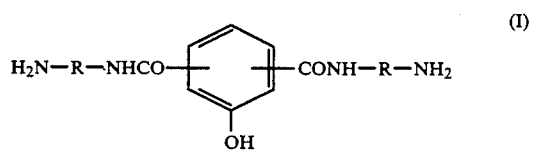

wherein R is a $C_1$-$C_{12}$ alkylene group which is unsubstituted or substituted, a group of formula (II) below

where $R^1$ and $R^2$, which are the same or different, each represents a hydrogen atom, a lower alkyl group, a halogen atom, a nitrile group, a nitro group, an alkoxy group, or a hydroxyl group, or a group of formula (III) below

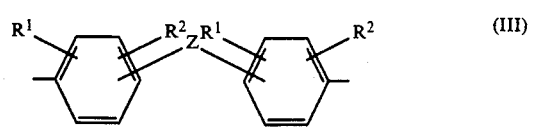

where $R^1$ and $R^2$ have the same meanings as defined above; and

Z is a simple chemical bond, —O—, >C=O, —CH$_2$—, —S—, —SO—, or —SO$_2$—, which comprises reducing a dinitro compound of general formula (IV) below

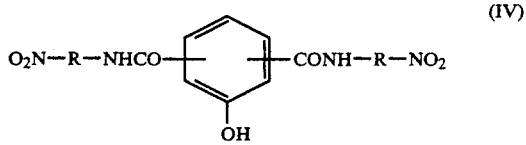

wherein R has the same meaning as defined above.

Furthermore, the present invention provides a polyamideimide resin having a repeating unit represented by general formula (V) below:

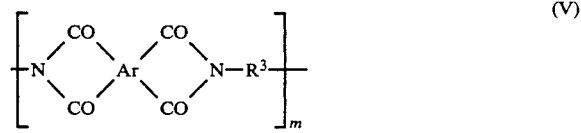

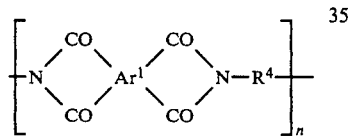

wherein Ar and $Ar^1$, which are the same or different, each represents a tetravalent aromatic residue to which two pairs of carbonyl groups are attached directly at four carbon atoms thereof, respectively, the two carbonyl groups in each one of the two pairs of carbonyl groups being attached to neighboring carbon atoms; $R^3$ is a group of general formula (VI) below:

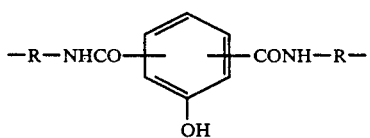

wherein R has the same meaning as defined above; $R^4$ is a divalent organic residue selected from aliphatic, aromatic and alicyclic groups other than those represented by $R^3$; is a positive integer and n is zero or a positive integer, provided that m and n satisfy m≧2n.

DETAILED DESCRIPTION OF THE INVENTION

Firstly, description will be made on the diamine compound of the present invention.

The diamine compound of the present invention includes those compounds represented by general formula (Ia) below:

wherein $R^{11}$ is a C$_1$-C$_{12}$ alkylene group which is unsubstituted or substituted, or a group of formula (II) below:

wherein $R^1$ and $R^2$ have the same meanings as defined above.

The diamine compound of the present invention also includes those compounds represented by general formula (Ib) below:

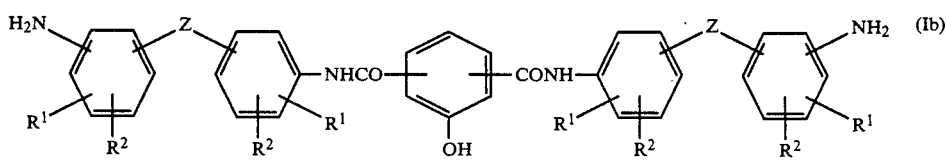

wherein $R^1$ and $R^2$ and Z have the same meanings as defined above.

Examples of the C$_1$-C$_{12}$ alkylene group represented by R include a methyl group, an ethyl group, a propyl group, a butyl group, a pentyl group, a hexyl group, an octyl group, a nonyl group, a decyl group, an undecyl group and a dodecyl group. These groups may contain normal, iso- and tertiary alkylene groups.

The group of general formula (II) represented by R includes the following groups:

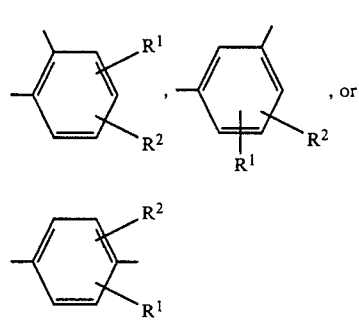

Examples of the lower alkyl group represented by $R^1$ and $R^2$ include alkyl groups preferably having 1 to 4 carbon atoms such as a methyl group, an ethyl group, a propyl group and a butyl group.

Examples of the alkoxy group represented by $R^1$ and $R^2$ include alkoxy groups preferably having 1 to 4 carbon atoms such as a methoxy group, an ethoxy group, a propoxy group and a butoxy group.

Examples of the halogen atoms represented by $R^1$ and $R^2$ include a fluorine atom, a chlorine atom, a bromine atom and an iodine atom.

Typical examples of the diamine compounds represented by general formula (Ia) above include N,N'-bis(2-aminophenyl)-5-hydroxyisophthalamide, N,N'-bis(3-aminophenyl)-5-hydroxyisophthalamide, N,N'-bis(4-aminophenyl)-5-hydroxyisophthalamide, N,N'-bis(2-aminophenyl)-2-hydroxyterephthalamide, N,N'-bis(3-aminophenyl)-2-hydroxyterephthalamide, N,N'-bis(4-aminophenyl)-2-hydroxyterephthalamide, N,N'-bis(2-aminophenyl)-2-hydroxyphthalamide, N,N'-bis(3-aminophenyl)-2-hydroxyphthalimide, N,N'-bis(4- aminophenyl)-2-hydroxyphthalamide, N,N'-bis(2-aminophenyl)-3-hydroxyphthalamide, N,N'-bis(3-aminophenyl)-3-hydroxyphthalamide, N,N'-bis-(4-aminophenyl)-3-hydroxyphthalamide, N,N'-bis(4-amino-3,5-dimethylphenyl)-5-hydroxyisophthalamide, N,N'-bis(4-amino-3,5-dimethylphenyl)-2-hydroxyterephthalamide, N,N'-bis(4-amino-3,5-dimethylphenyl)-2-hydroxyphthalamide, N,N'-bis(4-amino-3,5-dimethylphenyl)-3-hydroxyphthalamide, N,N'-bis(4-amino-n-butyl)-5-hydroxyisophthalamide, N,N'-bis(6-amino-n-hexyl)-5-hydroxyisophthalamide, N,N'-bis(4-amino-n-dodecyl)-5-hydroxyisophthalamide, and the like.

Typical examples of the diamine compounds represented by general formula (Ib) above include N,N'-bis[4-(4-amino-phenyoxy)phenyl]-4-or -5-hydroxyisophthalamide, N,N'-bis[4-4-aminophenylsulfinyl)phenyl]-4-or -5-hydroxyisophthalamide, N,N'-bis[4-(4-aminophenylsulfenyl)phenyl]-4- or -5-hydroxyisophthalamide, N,N'-bis-[4-(4-aminophenylsulfonyl)phenyl]-4-or -5-hydroxyisophthalamide, N,N'-bis[4-(4-aminophenyl)phenyl[-4-or -5-hydroxyisophthalmamide, N,N'-bis[4-(4-aminobenzoyl)phenyl]-4-or -5-hydroxyisophthalamide, N,N'-bis[4-(4-aminobenzyl)phenyl]-4- or -5-hydroxyisophthalamide, N,N'-bis[3-(3-aminophenyoxy)phenyl]-5-hydroxyisophthalamide, N,N'-bis[3-(3-aminophenylsulfinyl)phenyl[-5-hydroxyisophthalamide, N,N'-bis[3-(3-aminophenylsulfenyl)phenyl]-5-hydroxyisophthalamide, N,N'-bis[3-(3-aminophenylsufonyl)phenyl-5-hydroxyisophthalamide, N,N'-bis[3-(3-aminophenyl)phenyl]-5-hydroxyisophthalamide, N,N'-bis[3-(3 -aminobenzoyl)phenyl]-5-hydroxyisophthalamide, N,N'-bis[3-(3-aminobenzyl)phenyl]-5-hydroxyisophthalamide, N,N'-bis[4-(4-aminophenoxy)phenyl]-2-hydroxyterephthalamide, N,N'-bis[4-(4-aminophenylsulfinyl)phenyl]-2-hydroxyterephthalamide, N,N'-bis[4-(4-aminophenylsulfenyl)phenyl]-2-hydroxyterephthalamide, N,N'-bis[4-(4-aminophenylsulfonyl)phenyl]-2-hydroxyterephthalamide, N,N'-bis-[4-(4-aminophenyl)phenyl]-2-hydroxyterephthalamide, N,N'-bis[4-(4-aminobenzoyl)phenyl]-2-hydroxyterephthalamide, N,N'bis[4-(4-aminobenzyl)phenyl]-2-hydroxyterephthalamide, N,N'-bis[3-(4-aminophenoxy)-4-methylphenyl]-5-hydroxyisophthalamide, N,N'-bis-[4-(3-amino-6-methylphenoxy)phenyl]-5-hydroxyisophthalamide, N,N'-bis[3-(3-amino-6- methylphenoxy)-6-methylphenyl]-5-hydroxyisophthalamide, and the like.

The diamine compound represented by general formula (I) can be produced by reducing a dinitro compound represented by general formula (IV) below.

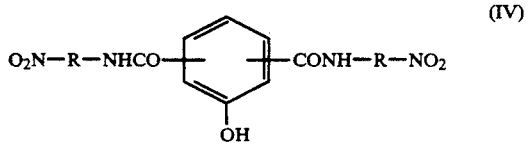

(IV)

wherein R has the same meaning as defined above.

The dinitro compound represented by general formula (IV) above can be produced by reacting a dicarboxylic acid of formula (V) below:

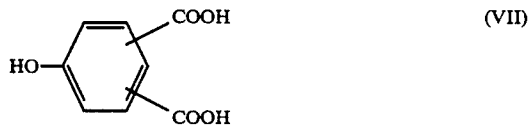

(VII)

with a nitroamine compound represented by general formula (VIII) below:

$$H_2N-R-NO_2 \quad \text{(VIII)}$$

wherein R has the same meaning as defined above.

Examples of the dicarboxylic acid of formula (V) above and derivatives thereof are, for example, 2-hydroxyisophthalic acid, 4-hydroxyisophthalic acid, 5-hydroxyisophthalic acid, 2-hydroxyterephthalic acid, 3-hydroxyphthalic acid, 4-hydroxyphthalic acid, and their derivatives such as acid halides, esters, etc.

Of the nitroamine compounds of general formula (VIII), those in which R is a $C_1$-$C_{12}$ alkylene group which is unsubstituted or substituted, or a group of formula (II) above, i.e., nitroamine compounds of general formula (VIIIa) below:

$$H_2N-R^{11}-NO_2 \quad \text{(VIIIa)}$$

wherein $R^{11}$ has the same meaning as defined above, are known compounds, and examples thereof include o-, m- or p-nitroaniline, 3,4- 4,5- or 3,5-dimethyl-2-nitroaniline, 4,5- 4,6-dimethyl-3-nitroaniline, 3,5-dimethyl-4-nitroaniline, 4-nitro-n-butylamine, 6nitro-n-hexylamine, 12-nitro-n-dodecylamine, 2,2-dimethyl-3-nitropropylamine, and the like.

On the other hand, of the nitroamine compounds of formula (VIII), those in which R is a group of formula (III) above, i.e., nitroamine compounds represented by general formula (VIIIb) below:

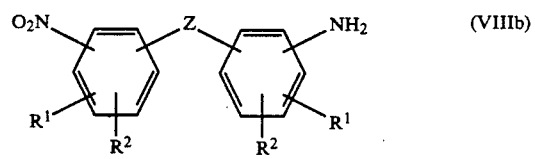

(VIIIb)

can be produced by various methods. Of the nitroamine compounds represented by general formula (VIIIb), those in which Z is an oxygen atom or a sulfur atom can be produced by a method of Williamson, for example, a method described in *Journal of Chemical Society*, Vol. 61, pp. 2764 (1939).

Those in which Z is —SO— or —SO₂— can be obtained by oxidizing the compounds of general formula (VIIIb) in which Z is a sulfur atom. In this case, there can be used an oxidizing agent such as hydrogen peroxide, sodium periodate and the like. The nitroamine compounds of general formula (VIIIb) in which Z is —SO— can be produced by oxidizing with hydrogen peroxide, for example, at low temperatures. On the other hand, those in which Z is —SO₂— can be obtained by performing the oxidation reaction at high temperatures.

The nitroamine compounds represented by general formula (VIIIb) in which Z is a simple chemical bond, —CO— or —CH₂— can be produced by a method of Friedel Crafts, for example, a method described in *Chemishe Berichte*, Vol. 17, pp. 419 and pp. 2320 (1884).

More particularly, the nitroamine compounds represented by general formula (VIIIb) in which Z is an oxygen atom can be obtained by reacting an aminophenol derivative with a halogenated nitrobenzene derivative. Examples of the aminophenol derivatives include o-, m- or p-aminophenol, 2-, 3- or 5-methyl-4-aminophenol, 4-methyl-3-aminophenol, 3,5- or 2,6-dimethyl-4-aminophenol, 3- or 5-n-butyl-4-aminophenol, 5-amino-2-methylphenol, and their derivatives. Examples of the halogenated nitrobenzene derivatives include o-, m- or p-chloronitrobenzene, 2- or 3-methyl-4-chloronitrobenzene, 3-, 4-, 5- or 6-methyl-2chloronitrobenzene, 2,6- or 3,5-dimethyl-4-chloronitrobenzene, 2- or 3-n-butyl-4-chloronitrobenzene, 2-chloro-4nitrotoluene, and their derivatives.

It is preferred that the reaction between the aminophenol derivative and the halogenated nitrobenzene derivative be carried out in a solvent in the presence of an inorganic or organic base such as sodium hydroxide, potassium hydroxide, sodium amide, potassium carbonate, sodium carbonate, triethylamine, barium oxide, silver oxide or sodium hydride. Alternatively, the amiophenol derivative can be converted into its corresponding phenoxide before it is reacted with the halogenated nitrobenzene derivative in a solvent.

Examples of the solvent which can be used in the reaction between the aminophenol derivative or its phenoxide and the halogenated nitrobenzene derivative include toluene, benzene, tetrahydrofuran, acetone, diethyl ether, water, methanol, ethanol, butanol, dimethylformamide, dimethylacetamide, dimethyl sulfoxide, and the like.

The reaction can proceed usually in a temperature range of from room temperature to reflux temperature, and preferably from 80° C. to 130° C. Usually, the reaction is completed in from several minutes to 24 hours.

The nitroamine compounds produced can be isolated as precipitates by pouring the reaction mixture in water after concentrating it. After the isolation, it can be subjected to washing, drying and other operations usually used.

Reaction between the nitroamine compound of general formula (VIII) with the dicarboxylic acid of formula (V) or its derivative is carried out usually in a solvent in the presence of a condensing agent.

As for the solvent which can be used, there can be cited, for example, toluene, benzene, chlorobenzene, dichlorobenzene, acetonitrile, pyridine, tetrahydrofuran, acetic anhydride, dichloromethane, hexane, cyclohexane, dimethylformamide, dimethylacetamide, dimethyl sulfoxide, N-methyl-2-pyrrolidone, hexamethylphosphoric triamide, and the like.

If desired, inorganic salts such as lithium chloride and calcium chloride can be added to the reaction system in order to increase solvating ability of the protic solvents used or inhibit side reactions which would otherwise tend to occur.

As for the condensing agent, there can be used, for example, triphenyl phosphite, diphenyl phosphite, tri-o-tollyl phosphite, di-o-tollyl phosphite, tri-m-tollyl phosphite, di-m-tollyl phosphite, tri-p-tollyl phosphite, di-p-tollyl phosphite, di-o-chlorophenyl phosphite, tri-p-chlorophenyl phosphite, di-p-chlorophenyl phosphite, dicyclohexylcarbodiimide, triphenyl phosphate, diphenyl phosphonate, and the like.

The reaction is continued preferably at a temperature of from 60° C. to 150° C. for a period of from several minutes to 24 hours.

If desired, the reaction can proceed under different conditions described above. For example, it can be carried out in the presence of excess amount of nitroamines, in solvents at high temperatures, or with removing water to be formed in order to shift equilibrium to the side of production of dinitro compounds.

The dinitro compounds of general formula (IV) can be isolated as precipitates by pouring the reaction mixture in methanol. After the isolation, the precipitates can be subjected to further operations such as washing, drying and the like usually used.

Alternatively, the dinitro compounds represented by general formula (IV) in which R is a $C_1$-$C_{12}$ alkylene group which is unsubstituted or substituted, or a group of formula (II) above, i.e., nitroamine compounds of general formula (VIIIa) above, can be produced by reaction between an acid halide and an amine as described, for example, in *Journal of Organic Chemistry*, Vol. 32, pp. 3069 (1967), reaction between a carboxylic acid and an isocyanate as described, for example, in *Chemical Reviews*, Vol. 57, pp. 47 (1957), reaction between an ester and an amine as described, for example, in *Tetrahedron Letters*, pp. 1791 (1970), and the like.

Reduction of the dinitro compounds of general formula (IV) can be carried out by catalytic reduction (catalytic hydrogenation), acidic reduction, basic reduction and the like.

The catalytic hydrogenation can usually be performed in a solvent using a catalyst in hydrogen gas atmosphere.

Examples of the catalyst which can be used in the catalytic hydrogenation include metal catalysts such as palladium carbon, strontium carbonate with palladium, sodium borohydride with palladium, platinum (IV) oxide, Raney nickel, and rhenium oxide. The amount of the metal catalyst to be used is preferably 5 to 10% by weight based on the weight of the dinitro compound to be reduced.

As for the solvent which can be used in the catalytic hydrogenation, there can be cited, for example, ethanol, methanol, acetic acid, dioxane, cyclohexane, water, tetrahydrofuran, ethyl acetate, dimethylformamide, and the like. Particularly preferred is dimethylformamide.

The reaction temperature is usually from room temperature to reflux temperature, preferably from 25° C. to 50° C. The reaction is usually completed in from 4 to 48 hours.

The diamine compounds of general formula (I) produced can be obtained as precipitates in an aqueous solution and purified by recrystallization from methanol.

The diamine compounds of the present invention are useful as a monomer for producing high polymers which have active sites for reactive compounds, particularly epoxy compounds.

Next, description will be made on the polyamideimide resin of the present invention.

In general formula (VI), examples of the tretravalent organic residue represented by Ar and $Ar^1$ include tetravalent aliphatic residues, aromatic residues and alicyclic residues, preferably aromatic residues such as the following groups:

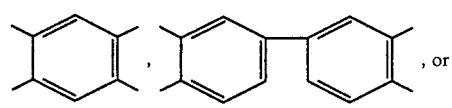

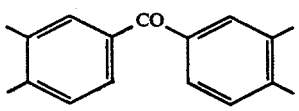

The polyamideimide resin of the present invention which has a repeating unit represented by general formula (V) includes a polyamideimide resin having a repeating unit represented by general (Va) below:

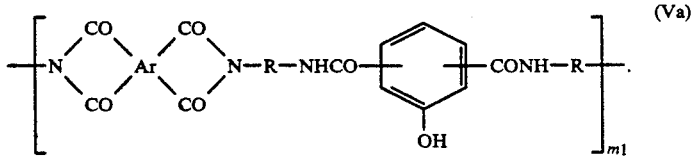

wherein R and Ar have the same meanings as defined above; and $m_1$ is a positive integer.

Also, it includes a polyamideimide resin represented by general formula (Vb) below:

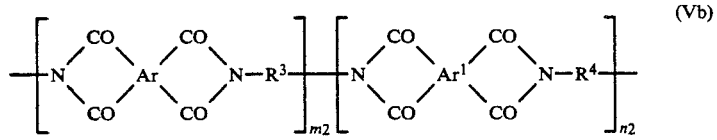

wherein Ar, $Ar^1$, $R^3$ and $R^4$ have the same meanings as defined above, and $m_2$ and $n_2$ are each a positive integer satisfying relationship: $m_2 \geq 2n_2$.

The polyamideimide resin of the present invention represented by general formula (Va) can be produced by condensation polymerization (polycondensation) between the diamine compounds of general formula (I) of the present invention with a tetracarboxylic acid dianhydride or its derivative. Examples of the diamine compound of general formula (I) are cited hereinabove.

As for the tetracarboxylic dianhydride, there can be cited, for example, pyromellitic dianhydride, 2,3,6,7-naphthalenetetracarboxylic dianhydride, 3,4,3',4'-biphenyltetracarboxylic dianhydride, 2,3,2',3'-biphenyltetracarboxylic dianhydride, bis(3,4-dicarboxyphenyl)methane dianhydride, bis(3,4-dicarboxyphenyl) ether dianhydride, bis(3,4-dicarboxyphenyl)sulfone dianhydride, 2,2-bis(3,4-dicarboxyphenyl)propane dianhydride, 3,4,3',4'-benzophenonetetracarboxylic dianhydride, butanetetracarboxylic dianhydride, 4,4'-biphthalic dianhydride, 2,2-bis(3,4-dicarboxyphenyl)-1,1,1,3,3,3,-hexafluoropropane dianhydride and the like.

The polyamideimide resin of the present invention represented by general formula (Vb) above can be produced by copolymerizing the diamine compound of general formula (I) and other diamine compound with the tetracarboxylic dianhydride. Examples of the other diamine compound include N,N'-bis(2-, 3- or 4-aminophenyl)isophthalamide, N,N'-bis(2-, 3- or 4-aminophenyl)terephthalamide, N,N'bis(2-aminophenyl)phthalamide, N,N'-bis(4-amino-3,5-dimethylphenyl)isophthalamide, N,N'-bis(4-amino-3,5-dimethylphenyl)terephthalamide, N,N'-bis(4-amino-3,5-dimethylphenyl)phthalamide, N,N'-bis(4-amino-n-butyl)-isophthalamide, N,N'-bis(6-amino-n-hexyl)isophthalamide, N,N'-bis(12-amino-n-dodecyl)isophthalamide, m- or p-phenylenediamine, m-tollylenediamine, 4,4,'-, 3,3'- or 3,4'-diaminodiphenyl ether, 4,4'- or 3,3'-diaminodiphenyl thioether, 3,3'-dimethyl-4,4'-diaminodiphenyl thioether, 3,3'-diethoxy-4,4'-diaminodiphenyl thioether, 4,4'-diaminobenzophenone, 3,3'-dimethyl-4,4'-diaminobenzophenone, 3,3'- or 4,4'-diaminodiphenylmethane, 3,3'-dimethoxy-4,4'-diaminodiphenylmethane, 2,2'-bis(3- or 4aminophenyl)propane, 4,4'-diaminodiphenyl sulfoxide, 3,3'- or 4,4'-diaminodiphenylsulfone, benzidine, 3,3'-dimethylbenzidine, 3,3'-dimethoxybenzidine, 3,3'-diaminobiphenyl, 2,2-bis[4-(4-aminophenoxy)phenyl]propane, 2,2-bis[3-methyl4-(4-aminophenoxy)phenyl]propane, 2,2-bis[3-chloro-4-(4aminophenoxy)phenyl]propane, 2,2-bis[3,5-dimethyl-4-(4aminophenoxy)phenyl]propane, 1,1-bis[4-(4-aminophenoxy)phenyl]ethane, 1,1-bis[3-chloro-4-(4-aminophenoxy)phenyl]ethane, bis[4-(4-aminophenoxy)phenyl]methane, bis[3-methyl4-(4-aminophenoxy)phenyl]methane, piperazine, hexamethylenediamine, heptamethylenediamine, tetramethylenediamine, p- or m-xylylenediamine, 3-methylheptamethylenediamine, and the like.

The reaction between the diamine compound of general formula (I) and the tetracarboxylic dianhydride or its derivative can be performed by known methods. For example, 1 equivalent of a diamine compound is compounded with 0.8 to 1.3 equivalents of a tetracarboxylic dianhydride in an inert polar organic solvent, and the mixture is reacted at a temperature of $-20°$ C. to $+150°$ C., preferably $0°$ C. to $60°$ C., for several tens minutes to several days to form a polyamic acid, which is then imidated, thus producing the polyamideimide resin of the present invention.

As for the inert polar organic solvent, there can be acetamide, N-methyl-2-pyrrolidone, N-methylcarprolactam, dimethyl sulfoxide, tetramethylurea, pyridine, dimethylsulfone, hexamethylphosphoric triamide, and the like.

Imidation reaction can be performed by thermal dehydration-cyclization with heating or chemical dehydration-cyclization using a dehydration-cyclization catalyst.

When dehydration-cyclization is performed thermally, the reaction temperature is usually from 150° C. to 400° C., preferably from 180° C. to 350° C. The reaction time is usually from 30 seconds to 10 hours, preferably from 5 minutes to 5 hours.

In the case where a dehydration-cyclization catalyst is used, the reaction temperature is usually from 0° C. to 180° C., preferably, from 10° C. to 80° C. The reaction time is usually from several tens minutes to several days, preferably from 2 to 12 hours. As for the dehydration-cyclization catalyst, there can be cited, for example, acetic acid, propionic acid, lactic acid, benzoic acid and the like. In this case, it is preferred to use a cyclization promoting compound, for example, pyridine, together with the catalyst. The amount of the dehydration-cyclization catalyst to be used is no less than 200 mol%, preferably form 300 to 1,000 mol%, based on the total amount of the diamine compound used. Furthermore, the cyclization promoting compound is used in an amount of 150 to 500 mol% based on the total amount of the diamine compound used.

The polyamideimide resin of the present invention having a repeating unit represented by general formula (V) above has an intrinsic viscosity (N-methyl-2-pryrolidone, concentrations: 0.5 g/dl, 30° C.) of from 0.1 to 5.0 dl/g, preferably from 0.2 to 1.5 dl/g.

The polyamide resin of the present invention is excellent in heat resistance and solubility in solvents and can be blended with other reactive resins uniformly. It is useful as films, coverings for electric wires, adhesives, paints, raw material for laminates and the like which are to be used as high temperatures.

EXAMPLES

The present invention will be described in greater detail with reference to examples. However, the present invention should not be construed as being limited thereto.

EXAMPLE 1

(A) N,N'-Bis(3-nitrophenyl)-5-hydroxyisophthalamide

To a solution of 27.6 g (200 mmol) of m-nitroaniline and 18.2 g (100 mmol) of 5-hydroxyisophthalic acid in 200 ml of N-methyl-2-pyrrolidone, there were added 50 ml of pyridine, 62 g (200 mmol) of triphenyl phosphite and 10.6 g (250 mmol) of lithium chloride serially, and the resulting mixture was stirred at 100° C. for 6 hours. After standing to cool, the reaction mixture was poured in 3,000 ml of methanol and stirred at room temperature for 1 hour. Solids which separated out were filtered out. After washing with hot methanol, the solids were dried to give 33.7 g (yield: 80%) of the above-named compound.

| Elemental Analysis Values for $C_{20}H_{14}N_4O_7$ | | | |
| --- | --- | --- | --- |
| | C | H | N |
| Calculated (%): | 56.88 | 3.34 | 13.27 |
| Found (%): | 56.79 | 3.31 | 13.29 |

IR Spectral Analysis (cm$^{-1}$:KBr method)
3520, 1660, 1528, 1350
1H-NMR Spectral Analysis ($\delta$:DMSO-d$^6$, TMS standard)
7.53–8.86 (11H, m), 10.90 (2H, s)

(B) N,N'-Bis(3-aminophenyl)-5-hydroxyisophthalamide

A suspension of 20 g (48 mmol) of the product in (A), 2 g of palladium carbon and 150 ml of dimethylformamide was heated at 50° C. for 12 hours in hydrogen gas atmosphere. After removing palladium carbon by filtration, the filtrate was poured in 1,000 ml of water. The solids which separated out were filtered out. After drying, the solids were extracted with methanol using a Soxhlet apparatus. Methanol was distilled off from the extract under reduced pressure to give 15.4 g (yield: 88%) of the objective compound.

| Elemental Analysis Values for $C_{20}H_{18}N_4O_3$ | | | |
| --- | --- | --- | --- |
| | C | H | N |
| Calculated (%): | 66.29 | 5.01 | 15.46 |
| Found (%): | 66.40 | 4.99 | 15.50 |

IR Spectral Analysis (cm$^{-1}$:KBr method)
3203, 1660
1H-NMR Spectral Analysis ($\delta$:DMSO-d$^6$, TMS standard)
3.40 (4H, bs), 6.13–7.93 (11H, m), 10.00 (2H, s)

EXAMPLE 2

(A) N,N'-Bis(4-nitrophenyl)-5-hydroxyisophthalamide

To a solution of 27.6 g (200 mmol) of p-nitroaniline and 18.2 g (100 mmol) of 5-hydroxyisophthalic acid in 200 ml of N-methyl-2-pyrrolidone, there were added 50 ml of pyridine, 62 g (200 mmol) of triphenyl phosphite and 10.6 g (250 mmol) of lithium chloride serially, and the resulting mixture was stirred at 100° C. for 6 hours. Then, the same procedures as in Example 1 (A) were repeated to obtain 35.2 g (yield: 83%) of the above-named compound.

| Elemental Analysis Values for $C_{20}H_{14}N_4O_7$ | | | |
| --- | --- | --- | --- |
| | C | H | N |
| Calculated (%): | 56.88 | 3.34 | 13.27 |
| Found (%): | 57.01 | 3.39 | 14.03 |

IR Spectral Analysis (cm$^{-1}$:KBr method)
3255, 1652, 1524, 1346
1H-NMR Spectral Analysis ($\delta$:DMSO-d$^6$, TMS standard)
7.42–8.91 (11H, m), 11.02 (2H, s)

(B) N,N'-Bis(4-aminophenyl)-5-hydroxyisophthalamide

A suspension of 20 g (48 mmol) of the product in (A), 2 g of palladium carbon and 150 ml of dimethylformamide was heated at 50° C. for 12 hours in hydrogen gas atmosphere. Then, the same procedures as in Example 1 (B) were repeated to obtain 15.0 g (yield: 85%) of the objective compound.

| Elemental Analysis Values for $C_{20}H_{18}N_4O_3$ | | | |
| --- | --- | --- | --- |
| | C | H | N |
| Calculated (%): | 66.29 | 5.01 | 15.46 |
| Found (%): | 66.22 | 5.05 | 15.41 |

IR Spectral Analysis (cm$^{-1}$:KBr method)
3211, 1661
1H-NMR Spectral Analysis ($\delta$:DMSO-d$^6$, TMS standard)
3.45 (4H, bs), 6.08–8.01 (11H, m), 10.05 (2H, s)

EXAMPLE 3

(A)
N,N'-Bis(6-nitro-n-hexyl)-5-hydroxyisophthalamide

To a solution of 29.2 g (200 mmol) of 6-nitro-n-hexylamine and 18.2 g (100 mmol) of 5-hydroxyisophthalic acid in 200 ml of N-methyl-2-pyrrolidone, there were added 50 ml of pyridine, 62 g (200 mmol) of triphenyl phosphite and 10.6 g (250 mmol) of lithium chloride serially, and the resulting mixture was stirred at 100° C. for 6 hours. Then, the same procedures as in Example 1

(A) were repeated to obtain 34.6 g (yield: 79%) of the above-named compound.

| Elemental Analysis Values for $C_{20}H_{30}N_4O_7$ | | | |
| --- | --- | --- | --- |
| | C | H | N |
| Calculated (%): | 54.79 | 6.90 | 12.78 |
| Found (%): | 56.01 | 6.95 | 12.76 |

IR Spectral Analysis (cm$^{-1}$:KBr method)
3240, 1645, 1526, 1341

1H-NMR Spectral Analysis ($\delta$:DMSO-d$^6$, TMS standard)
1.52 (12H, s), 7.52-8.82 (11H, m), 10.98 (2H, s)

(B) N,N'-Bis(6-amino-n-hexyl)-5-hydroxyisophthalamide

A suspension of 21 g (48 mmol) of the product in (A), 2.1 g of palladium carbon and 150 ml of dimethylformamide was heated at 50° C. for 12 hours in hydrogen gas atmosphere. Then, the same procedures as in Example 1 (B) were repeated to obtain 14.9 g (yield: 82%) of the objective compound.

| Elemental Analysis Values for $C_{20}H_{34}N_4O_3$ | | | |
| --- | --- | --- | --- |
| | C | H | N |
| Calculated (%): | 63.46 | 9.05 | 14.80 |
| Found (%): | 63.37 | 9.04 | 14.74 |

IR Spectral Analysis (cm$^{-1}$:KBr method)
3211, 1661

1H-NMR Spectral Analysis ($\delta$:DMSO-d$^6$, TMS standard)
1.50 (12H, s), 2.71 (4H, bs), 6.51-7.88 (11H, m), 10.25 (2H, s)

EXAMPLE 4

(A) 4-Nito-4'-aminodiphenyl ether

An aqueous solution of 42.7 g (326 mmol) of sodium p-aminophenoxide and 12.8 g (81 mmol) of p-chloronitrobenzene in 200 ml of water was refluxed for 8 hours. After removing unused p-chloronitrobenzene by steam distillation, solids which separated out were filtered and recrystallized from methanol to give 14.5 g (yield: 78%) of 4-nitro-4'aminodiphenyl ether.

| Elemental Analysis Values for $C_{12}H_{10}N_2O_3$ | | | |
| --- | --- | --- | --- |
| | C | H | N |
| Calculated (%): | 62.61 | 4.38 | 12.17 |
| Found (%): | 62.59 | 4.41 | 12.12 |

IR Spectral Analysis (cm$^{-1}$:KBr method)
1524, 1348

1H-NMR Spectral Analysis ($\delta$:DMSO-d$^6$, TMS standard)
3.50 (2H, s), 6.52-8.23 (8H, m)

(B) N,N'-Bis[4-(4-nitrophenoxy)phenyl]-5-hydroxyisophthalimide

To a solution of 46 g (200 mmol) of 4-nitro-4'aminodiphenyl ether and 18.2 g (100 mmol) of 5-hydroxyisophthalic acid in 200 ml of N-methyl-2-pyrrolidone, there were added 50 ml of pyridine, 62 g (200 mmol) of triphenyl phosphite and 10.6 g (250 mmol) of lithium chloride serially, and the resulting mixture was stirred at 100° C. for 6 hours. After standing to cool, the reaction mixture was poured in 3,000 ml of methanol and stirred at room temperature for 1 hour. Solids which separated out were filtered out. After washing with hot methanol, the solids were dried to give 51.6 g (yield: 85%) of the above-named compound.

| Elemental Analysis Values for $C_{32}H_{22}N_4O_9$ | | | |
| --- | --- | --- | --- |
| | C | H | N |
| Calculated (%): | 63.37 | 3.56 | 9.24 |
| Found (%): | 63.31 | 3.48 | 9.33 |

IR Spectral Analysis (cm$^{-1}$:KBr method)
3255, 1667, 1520, 1348

1H-NMR Spectral Analysis ($\delta$:DMSO-d$^6$, TMS standard)
6.46-8.81 (19H, m), 11.10 (2H, s)

(C) N,N'-Bis[4-(4-aminophenoxy)phenyl]-5-hydroxyisophthalamide

A suspension of 29 g (48 mmol) of the product in (B) above, 2 g of palladium carbon and 150 ml of dimethylformamide was heated at 50° C. for 12 hours in hydrogen gas atmosphere. After removing palladium carbon by filtration, the filtrate was poured in 1,000 ml of water. The solids which separated out were filtered out. After drying, the solids were extracted with methanol using a Soxhlet apparatus. Methanol was distilled off from the extract under reduced pressure to give 17.8 g (yield: 68%) of the objective compound.

| Elemental Analysis Values for $C_{32}H_{26}N_4O_5$ | | | |
| --- | --- | --- | --- |
| | C | H | N |
| Calculated (%): | 70.32 | 4.79 | 10.25 |
| Found (%): | 70.25 | 4.71 | 10.19 |

IR Spectral Analysis (cm$^{-1}$:KBr method)
3213, 1659

1H-NMR Spectral Analysis ($\delta$:DMSO-d$^6$, TMS standard)
3.46 (4H, s), 6.41-8.33 (19H, m), 9.98 (2H, s)

EXAMPLE 5

(A) 4-Nito-4'-aminodiphenylsulfide

An aqueous solution of 48 g (326 mmol) of sodium p-aminothiophenoxide and 12.8 g (81 mmol) of p-chloronitrobenzene in 200 ml of water was refluxed for 8 hours. After removing unused p-chloronitrobenzene by steam distillation, solids which separated out were filtered and recrystallized from methanol to give 16 g (yield: 80%) of 4-nitro-4'-aminodiphenylsulfide.

| Elemental Analysis Values for $C_{12}H_{10}N_2O_2S_2$ | | | |
| --- | --- | --- | --- |
| | C | H | N |
| Calculated (%): | 58.52 | 4.09 | 11.38 |
| Found (%): | 58.62 | 3.99 | 11.34 |

IR Spectral Analysis (cm$^{-1}$:KBr method)
1550, 1338

1H-NMR Spectral Analysis ($\delta$:DMSO-d$^6$, TMS standard)
4.83 (2H, s), 6.55-8.00 (8H, m)

(B)
N,N'-Bis[4-(4-nitrosulfenyl)phenyl]-5-hydroxyisophthalimide

To a solution of 45.2 g (200 mmol) of 4-nitro-4'-aminodiphenylsulfide and 18.2 g (100 mmol) of 5-hydroxyisophthalic acid in 200 ml of N-methyl-2-pyrrolidone, there were added 50 ml of pyridine, 62 g (200 mmol) of triphenyl phosphite and 10.6 g (250 mmol) of lithium chloride serially, and the resulting mixture was stirred at 100° C. for 6 hours. After standing to cool, the reaction mixture was poured in 3,000 ml of water and stirred at room temperature for 1 hour. Solids which separated out were filtered out. After washing with hot methanol, the solids were dried to give 51 g (yield: 80%) of the above-named compound.

| Elemental Analysis Values for $C_{32}H_{22}N_4O_7S_2$ | | | |
| --- | --- | --- | --- |
| | C | H | N |
| Calculated (%): | 60.18 | 3.47 | 8.77 |
| Found (%): | 60.22 | 3.39 | 8.82 |

IR Spectral Analysis (cm$^{-1}$:KBr method)
3230, 1661, 1520, 1333
1H-NMR Spectral Analysis ($\delta$:DMSO-d$^6$, TMS standard)
6.98–8.22 (19H, m), 10.92 (2H, s)

(C)
N,N'-Bis[4-(4-aminophenylsulfenyl)phenyl]-5-hydroxyisophthalamide

A suspension of 30.6 g (48 mmol) of the product in (B) above, 2 g of palladium carbon and 150 ml of dimethylformamide was heated at 50° C. for 12 hours in hydrogen gas atmosphere. After removing palladium carbon by filtration, the filtrate was poured in 1,000 ml of water. The solids which separated out were filtered out. After drying, the solids were extracted with methanol using a Soxhlet apparatus. Methanol was distilled off from the extract under reduced pressure to give 16.7 g (yield: 60%) of the objective compound.

| Elemental Analysis Values for $C_{32}H_{26}N_4O_3S_2$ | | | |
| --- | --- | --- | --- |
| | C | H | N |
| Calculated (%): | 66.42 | 4.53 | 9.68 |
| Found: | 66.37 | 4.45 | 9.74 |

IR Spectral Analysis (cm$^{-1}$:KBr method)
3241, 1659
1H-NMR Spectral Analysis ($\delta$:DMSO-d$^6$, TMS standard)
4.69 (4H, bs), 6.88–8.25 (19H, m), 10.01 (2H, s)

EXAMPLE 6

(A) 4-Nito-4'-aminodiphenyl sulfoxide

A mixed solution of 24.6 g (100 mmol) of 4-nitro-4'-aminodiphenylsulfide obtained in Example 5, 17 g (155 mmol) of 31% hydrogen peroxide and 50 ml of acetone was left to stand at room temperature for 60 hours. After removing acetone under reduced pressure, solids which separated out were filtered. The solids obtained were washed with hot water and dried to give 16 g (yield: 61%) of 4-nitro-4'-aminodiphenyl sulfoxide.

| Elemental Analysis Values for $C_{12}H_{10}N_2O_3S$ | | | |
| --- | --- | --- | --- |
| | C | H | N |
| Calculated (%): | 54.59 | 3.84 | 10.68 |
| Found (%): | 54.50 | 3.99 | 10.69 |

IR Spectral Analysis (cm$^{-1}$:KBr method)
1559, 1325
1H-NMR Spectral Analysis ($\delta$:DMSO-d$^6$, TMS standard)
4.92 (2H, s), 6.85–8.42 (8H, m)

(B)
N,N'-Bis[4-(4-nitrophenylsulfinyl)phenyl]-5-hydroxyisophthalimide

To a solution of 52.5 g (200 mmol) of 4-nitro-4'aminodiphenyl sulfoxide and 18.2 g (100 mmol) of 5-hydroxyisophthalic acid in 200 ml of N-methyl-2-pyrrolidone, there were added 50 ml of pyridine, 62 g (200 mmol) of triphenyl phosphite and 10.6 g (250 mmol) of lithium chloride serially, and the resulting mixture was stirred at 100° C. for 6 hours. After standing to cool, the reaction mixture was poured in 3,000 ml of water and stirred at room temperature for 1 hour. Solids which separated out were filtered out. After washing with hot methanol, the solids were dried to give 53 g (yield: 79%) of the above-named compound.

| Elemental Analysis Values for $C_{32}H_{22}N_4O_9S_2$ | | | |
| --- | --- | --- | --- |
| | C | H | N |
| Calculated (%): | 57.31 | 3.31 | 8.35 |
| Found (%): | 57.37 | 3.39 | 8.41 |

IR Spectral Analysis (cm$^{-1}$:KBr method)
3256, 1639, 1528, 1337
1H-NMR Spectral Analysis ($\delta$:DMSO-d$^6$, TMS standard)
6.95–8.33 (19H, m), 11.02 (2H, s)

(C)
N,N'-Bis[4-(4-aminophenylsulfinyl)phenyl]-5-hydroxyisophthalamide

A suspension of 32.2 g (48 mmol) of the product in (B) above, 2.1 g of palladium carbon and 150 ml of dimethylformamide was heated at 50° C. for 12 hours in hydrogen gas atmosphere. After removing palladium carbon by filtration, the filtrate was poured in 1,000 ml of water. The solids which separated out were filtered out. After drying, the solids were extracted with methanol using a Soxhlet apparatus. Methanol was distilled off from the extract under reduced pressure to give 17 g (yield: 58%) of the above-named compound.

| Elemental Analysis Values for $C_{32}H_{26}N_4O_5S_2$ | | | |
| --- | --- | --- | --- |
| | C | H | N |
| Calculated (%) | 62.94 | 4.29 | 9.17 |
| Found (%) | 63.11 | 4.34 | 9.09 |

IR Spectral Analysis (cm$^{-1}$:KBr method)
3230, 1658
1H-NMR Spectral Analysis ($\delta$:DMSO-d$^6$, TMS standard)
4.88 (4H, s), 6.90–8.20 (19H, m), 10.11 (2H, s)

EXAMPLE 7

(A) 4-Nito-4,-aminodiphenylsulfone

To a solution of 24.6 g (100 mmol) of 4-nitro-4'-aminodiphenylsulfide obtained in Example 5 in 200 ml of glacial acetic acid was added 250 ml of 31% hydrogen peroxide, and the resulting mixture was heated under reflux for 1 hour. After leaving it to cool, excessive amount of iced water was added to the reaction mixture. Solids which separated out were filtered. The solids obtained were washed with hot water and dried to give 23.7 g (yield: 85%) of 4-nitro-4'-aminodiphenylsulfone.

| Elemental Analysis Values for $C_{12}H_{10}N_2O_3S$ | | | |
|---|---|---|---|
| | C | H | N |
| Calculated (%) | 51.79 | 3.62 | 10.07 |
| Found (%) | 51.81 | 3.67 | 10.00 |

IR Spectral Analysis (cm$^{-1}$:KBr method)
1549, 1320

1H-NMR Spectral Analysis ($\delta$:DMSO-d$^6$, TMS standard)
4.78 (2H, s), 6.95-8.52 (8H, m)

(B) N,N'-Bis[4-(4-nitrophenylsulfonyl)phenyl]-5-hydroxyisophthalimide

To a solution of 55.7 g (200 mmol) of 4-nitro-4'-aminodiphenylsulfone and 18.2 g (100 mmol) of 5-hydroxyisophthalic acid in 200 ml of N-methyl-2-pyrrolidone, there were added 50 ml of pyridine, 62 g (200 mmol) of triphenyl phosphite and 10.6 g (250 mmol) of lithium chloride serially, and the resulting mixture was stirred at 100° C. for 6 hours. After standing to cool, the reaction mixture was poured in 3,000 ml of water and stirred at room temperature for 1 hour. Solids which separated out were filtered out. After washing with hot methanol, the solids were dried to give 61.8 g (yield: 88%) of the above-named compound.

| Elemental Analysis Values for $C_{32}H_{22}N_4O_{11}S_2$ | | | |
|---|---|---|---|
| | C | H | N |
| Calculated (%) | 54.70 | 3.16 | 7.97 |
| Found (%) | 54.73 | 3.20 | 7.86 |

IR Spectral Analysis (cm$^{-1}$:KBr method)
3231, 1656, 1534, 1337

1H-NMR Spectral Analysis ($\delta$:DMSO-d$^6$, TMS standard)
7.20-8.39 (19H, m), 11.10 (2H, s)

(C) N,N'-Bis[4-(4-aminophenylsulfonyl)phenyl]-5-hydroxyisophthalamide

A suspension of 33.7 g (48 mmol) of the product in (B) above, 2.1 g of palladium carbon and 150 ml of dimethylformamide was heated at 50° C. for 12 hours in hydrogen gas atmosphere. After removing palladium carbon by filtration, the filtrate was poured in 1,000 ml of water. The solids which separated out were filtered out. After drying, the solids were extracted with methanol using a Soxhlet apparatus. Methanol was distilled off from the extract under reduced pressure to give 20 g (yield: 65%) of the above-named compound.

| Elemental Analysis Values for $C_{32}H_{26}N_4O_7S_2$ | | | |
|---|---|---|---|
| | C | H | N |
| Calculated (%) | 59.80 | 4.08 | 8.72 |
| Found (%) | 59.81 | 4.10 | 8.73 |

IR Spectral Analysis (cm$^{-1}$:KBr method)
3229, 1660

1H-NMR Spectral Analysis ($\delta$:DMSO-d$^6$, TMS standard)
4 69 (4H 7.22-8.45 (19H, m), 10.05 (2H, s)

EXAMPLE 8

(A) 4-Nitro-3'-amino-6'-methyldiphenyl ether

An aqueous solution of 40.1 g (326 mmol) of sodium 5-amino-2-methylphenoxide and 12.8 g (81 mmol) of p-chloronitrobenzene in 200 ml of water was refluxed for 8 hours. After removing unused p-chloronitrobenzene by steam distillation, solids which separated out were filtered and recrystallized from methanol to give 13.8 g (yield: 70%) of 4-nitro-3'-amino-6'-methyldiphenyl ether.

| Elemental Analysis Values for $C_{32}H_{12}N_2O_3$ | | | |
|---|---|---|---|
| | C | H | N |
| Calculated (%) | 63.93 | 4.95 | 11.47 |
| Found (%) | 62.69 | 4.43 | 12.01 |

IR Spectral Analysis (cm$^{-1}$:KBr method)
1537, 1344

1H-NMR Spectral Analysis ($\delta$:DMSO-d$^6$, TMS standard)
2.22 (3H, s), 3.53 (2H, s), 6.49-8.21 (7H, m)

(B) N,N'-Bis[3-(4-nitrophenoxy)-4-methylphenyl]-5-hydroxyisophthalimide

To a solution of 49 g (200 mmol) of 4-nitro-3'-amino-6'-methyldiphenyl ether and 18.2 g (100 mmol) of 5-hydroxyisophthalic acid in 200 ml of N-methyl-2-pyrrolidone, there were added 50 ml of pyridine, 62 g (200 mmol) of triphenyl phosphite and 10.6 g (250 mmol) of lithium chloride serially, and the resulting mixture was stirred at 100° C. for 6 hours. After standing to cool, the reaction mixture was poured in 3,000 ml of water and stirred at room temperature for 1 hour. Solids which separated out were filtered out. After washing with hot methanol, the solids were dried to give 51.5 g (yield: 89%) of the above-named compound.

| Elemental Analysis Values for $C_{32}H_{26}N_4O_9S_2$ | | | |
|---|---|---|---|
| | C | H | N |
| Calculated (%) | 66.43 | 4.35 | 9.68 |
| Found (%) | 66.31 | 4.55 | 9.39 |

IR Spectral Analysis (cm$^{-1}$:KBr method)
3248, 1658, 1526, 1340

1H-NMR Spectral Analysis ($\delta$:DMSO-d$^6$, TMS standard)
2.31 (6H, s), 6.51-8.78 (17H, m), 11.00 (2H, s)

(C)
N,N'-Bis[3-(4-aminophenoxy)-4-methylphenyl]-5-hydroxyisophthalamide

A suspension of 28 g (48 mmol) of the product in (B) above, 2 g of palladium carbon and 150 ml of dimethylformamide was heated at 50° C. for 12 hours in hydrogen gas atmosphere. After removing palladium carbon by filtration, the filtrate was poured in 1,000 ml of water. The solids which separated out were filtered out. After drying, the solids were extracted with methanol using a Soxhlet apparatus. Methanol was distilled off from the extract under reduced pressure to give 17.4 g (yield: 70%) of the objective compound.

| Elemental Analysis Values for $C_{32}H_{30}N_4O_5S_2$ | | | |
|---|---|---|---|
| | C | H | N |
| Calculated (%) | 74.11 | 5.83 | 10.80 |
| Found (%) | 74.31 | 5.69 | 10.68 |

IR Spectral Analysis (cm$^{-1}$:KBr method)
3225, 1649

1H-NMR Spectral Analysis (δ:DMSO-d$^6$, TMS standard)
2.25 (6H, s), 3.48 (4H, bs), 6.55–8.01 (19H, m), 10.03 (2H, s)

EXAMPLE 9

(A) 3-Nito-6-methyl-4'-aminodiphenyl ether

An aqueous solution of 40.1 g (326 mmol) of sodium p-aminophenoxide and 17.5 g (81 mmol) of 2-chloro-4-nitrotoluene in 200 ml of water was refluxed for 8 hours. After removing unused 2-chloro-4-nitrotoluene by steam distillation, solids which separated out were filtered and recrystallized from methanol to give 13.6 g (yield: 69%) of 3-nitro-6-methyl-4'-aminodiphenyl ether.

| Elemental Analysis Values for $C_{13}H_{12}N_2O_3$ | | | |
|---|---|---|---|
| | C | H | N |
| Calculated (%) | 63.93 | 4.95 | 11.47 |
| Found (%) | 64.21 | 5.05 | 11.99 |

IR Spectral Analysis (cm$^{-1}$:KBr method)
1536, 1350

1H-NMR Spectral Analysis (δ:DMSO-d$^6$, TMS standard)
2.23 (3H, s), 3.45 (2H, s), 6.39–8.36 (7H, m)

(B)
N,N'-Bis[4-(3-nitro-6-methylphenoxy)phenyl]-5-hydroxyisophthalimide

To a solution of 49 g (200 mmol) of 3-nitro-6-methyl-4'-aminodiphenyl ether and 18.2 g (100 mmol) of 5-hydroxyisophthalic acid in 200 ml of N-methyl-2-pyrrolidone, there were added 50 ml of pyridine, 62 g (200 mmol) of triphenyl phosphite and 10.6 g (250 mmol) of lithium chloride serially, and the resulting mixture was stirred at 100° C. for 6 hours. After standing to cool, the reaction mixture was poured in 3,000 ml of water and stirred at room temperature for 1 hour. Solids which separated but were filtered out. After washing with hot methanol, the solids were dried to give 49.2 g (yield: 85%) of the above-named compound.

| Elemental Analysis Values for $C_{32}H_{30}N_4O_9$ | | | |
|---|---|---|---|
| | C | H | N |
| Calculated (%) | 66.43 | 4.35 | 9.68 |
| Found (%) | 66.51 | 4.25 | 9.56 |

IR Spectral Analysis (cm$^{-1}$:KBr method)
3240, 1646, 1521, 1348

1H-NMR Spectral Analysis (δ:DMSO-d$^6$, TMS standard)
2.35 (6H, s), 6.48–8.68 (17H, m), 10.88 (2H, s)

(C)
N,N'-Bis[4-(3-amino-6-methylphenoxy)phenyl]-5-hydroxyisophthalamide

A suspension of 28 g (48 mmol) of the product in (B) above, 2 g of palladium carbon and 150 ml of dimethylformamide was heated at 50° C. for 12 hours in hydrogen gas atmosphere. After removing palladium carbon by filtration, the filtrate was poured in 1,000 ml of water. The solids which separated out were filtered out. After drying, the solids were extracted with methanol using a Soxhlet apparatus. Methanol was distilled off from the extract under reduced pressure to give 16.2 g (yield: 65%) of the objective compound.

| Elemental Analysis Values for $C_{32}H_{30}N_4O_5$ | | | |
|---|---|---|---|
| | C | H | N |
| Calculated (%) | 74.11 | 5.83 | 10.80 |
| Found (%) | 73.88 | 6.01 | 10.61 |

IR Spectral Analysis (cm$^{-1}$:KBr method)
3235, 1648

1H-NMR Spectral Analysis (δ:DMSO-d$^6$, TMS standard)
2.30 (6H, s), 3.45 (4H,bs), 6.48–8.25 (17H, m), 9.89 (2H, s)

EXAMPLE 10

(A) 3-Nitro-6-methyl-3'-amino-6-methyldiphenyl ether

An aqueous solution of 40.1 g (326 mmol) of sodium 5-amino-2-methylphenoxide and 17.5 g (81 mmol) of 2-chloro-4-nitrotoluene in 200 ml of water was refluxed for 8 hours. After removing unused 2-chloro-4-nitrotoluene by steam distillation, solids which separated out were filtered and recrystallized from methanol to give 15.2 g (yield: 73%) of 3-nitro-6-methyl-3'-amino-6-methyldiphenyl ether.

| Elemental Analysis Values for $C_{14}H_{14}N_2O_3$ | | | |
|---|---|---|---|
| | C | H | N |
| Calculated (%) | 65.11 | 5.46 | 10.85 |
| Found (%) | 64.92 | 5.29 | 11.02 |

IR Spectral Analysis (cm$^{-1}$:KBr method)
1540, 1343

1H-NMR Spectral Analysis (δ:DMSO-d$^6$, TMS standard)
2.15 (3H, s), 2.28 (3H, s), 3.49 (2H, s)m, 6.25–8.01 (6H, m)

(B)
N,N'-Bis[3-(3-nitro-6-methylphenoxy)-6-methylphenyl]-5-hydroxyisophthalimide To a solution of 51.6 g (200 mmol) of 3-nitro-6-methyl-3'-amino-6-methyldiphenyl ether and 18.2 g (100 mmol) of 5 hydroxyisophthalic acid in 200 ml of N-methyl-2-pyrrolidone, there were added 50 ml of pyridine, 62 g (200 mmol) of triphenyl phosphite and 10.6 g (250 mmol) of lithium chloride serially, and the resulting mixture was stirred at 100° C. for 6 hours. After standing to cool, the reaction mixture was poured in 3,000 ml of water and stirred at room temperature for 1 hour. Solids which separated out were filtered out. After washing with hot methanol, the solids were dried to give 49.1 g (yield: 82%) of the above-named compound.

| Elemental Analysis Values for $C_{34}H_{30}N_4O_9$ | | | |
| --- | --- | --- | --- |
|  | C | H | N |
| Calculated (%) | 67.32 | 4.98 | 9.24 |
| Found (%) | 67.18 | 5.06 | 9.32 |

IR Spectral Analysis (cm$^{-1}$:KBr method)
3245, 1651, 1530, 1342

1H-NMR Spectral Analysis (δ:DMSO-d$^6$, TMS standard)
2.24 (6H, s), 2.36 (6H, s), 6.39–8.55 (15H, m), 11.10 (2H, s)

(C)
N,N'-Bis[3-(3-amino-6-methylphenoxy)-6-methylphenyl]-5-hydroxyisophthalamide A suspension of 29 g (48 mmol) of the product in (B) above, 2 g of palladium carbon and 150 ml of dimethylformamide was heated at 50° C. for 12 hours in hydrogen gas atmosphere. After removing palladium carbon by filtration, the filtrate was poured in 1,000 ml of water. The solids which separated out were filtered out. After drying, the solids were extracted with methanol using a Soxhlet apparatus. Methanol was distilled off from the extract under reduced pressure to give 17.8 g (yield: 68%) of the objective compound.

| Elemental Analysis Values for $C_{34}H_{34}N_4O_5$ | | | |
| --- | --- | --- | --- |
|  | C | H | N |
| Calculated (%) | 74.70 | 6.27 | 10.25 |
| Found (%) | 74.65 | 6.21 | 10.53 |

IR Spectral Analysis (cm$^{-1}$:KBr method)
3226, 1643

1H-NMR Special Analysis (δ:DMSO-d$^6$, TMS standard)
2.24 (6H, s), 2.33 (6H, s), 3.55 (4H, s), 6.51–8.40 (15H, m), 10.00 (2H, s)

EXAMPLE 11

A solution of 18 g (50 mmol) of N,N'-bis(3-aminophenyl)-5-hydroxyisophthalamide and 16 g (50 mmol) of 3,4,3',4'-benzophenonetetracarboxylic dianhydride in 150 ml of N-methyl-2-pyrrolidone was reacted at room temperature for 6 hours in nitrogen atmosphere to give a polyamic acid solution. The polyamic acid solution is heated at 200° C. for 2 hours to perform hydration-cyclization reaction. After cooling, the resulting polymer solution was poured in a large amount of methanol. Solids which separated out were filtered and the solids were washed and dried to give a polymer having an intrinsic viscosity of 0.65 dl/g (N-methyl-2-pyrrolidone, concentration: 0.5 g/dl, 30° C., hereafter the same).

Infrared spectral analysis showed absorption at 3227 cm$^{-1}$ ascribable to phenolic hydroxyl group, absorptions at 1724 cm$^{-1}$ and 1779 cm$^{-1}$ ascribable to imide bonds, absorption at 1677 cm$^{-1}$ ascribable to carbonyl group in amide bonds. These results confirmed that the product is a polyamideimide having a repeating unit as shown in Table below.

EXAMPLE 12

Substantially the same procedures as in Example 11 were repeated except that 18 g (50 mmol) of N,N-bis(4-aminophenyl)-5-hydroxyisophthalamide was used in place of N,N-bis(3-aminophenyl)-5-hydroxyisophthalamide to give a polyamideimide resin having an intrinsic viscosity of 0.58 dl/g.

Similar tests as in Example 11 confirmed that the resin has a repeating unit shown in Table below.

EXAMPLE 13

Substantially the same procedures as in Example 11 were repeated except that 11 g (50 mmol) of pyromellitic dianhydride was used in place of 3,4,3',4'-benzophenonetetracarboxylic dianhydride to give a polyamideimide resin having an intrinsic viscosity of 0.49 dl/g.

Similar tests as in Example 11 confirmed that the resin has a repeating unit shown in Table below.

EXAMPLE 14

Substantially the same procedures as in Example 11 were repeated except that 18 g (50 mmol) of N,N-bis(4-aminophenyl)-5-hydroxyisophthalamide and 11 g (50 mmol) of pyromellitic dianhydride were used in place of N,N-bis(3-aminophenyl)-5-hydroxyisophthalamide and 3,4,3',4'-benzophenonetetracarboxylic dianhydride, respectively, to give a polyamideimide resin having an intrinsic viscosity of 0.51 dl/g. Similar tests as in Example 11 confirmed that the resin has a repeating unit shown in Table below.

EXAMPLE 15

Substantially the same procedures as in Example 11 were repeated except that 15 g (50 mmol) of 4,4'-biphthalic dianhydride was used in place of 3,4,3',4'-benzophenonetetracarboxylic dianhydride to give a polyamideimide resin having an intrinsic viscosity of 0.68 dl/g.

Similar tests as in Example 11 confirmed that the resin has a repeating unit shown in Table below.

EXAMPLE 16

Substantially the same procedures as in Example 11 were repeated except that 18 g (50 mmol) of N,N-bis(4-aminophenyl)-5-hydroxyisophthalamide and 15 g (50 mmol) of 4,4'-biphthalic dianhydride were used in place of N,N-bis(3-aminophenyl)-5-hydroxyisophthalamide and 3,4,3',4'-benzophenonetetracarboxylic dianhydride, respectively, to give a polyamideimide resin having an intrinsic viscosity of 0.60 dl/g. Similar tests as in Example 11 confirmed that the resin has a repeating unit shown in Table below.

EXAMPLE 17

Substantially the same procedures as in Example 11 were repeated except that 19.5 g (50 mmol) of N,N-bis(3-amino-2-methylphenyl)-5-hydroxyisophthalamide was used in place of N,N-bis(3-aminophenyl)-5-hydroxyisophthalamide to give a polyamideimide resin having an intrinsic viscosity of 0.46 dl/g.

Similar tests as in Example 11 confirmed that the resin has a repeating unit shown in Table below.

EXAMPLE 18

Substantially the same procedures as in Example 11 were repeated except that 19.5 g (50 mmol) of N,N-bis(3-amino-2-methylphenyl)-5-hydroxyisophthalamide and 11 g (50 mmol) of pyromellitic dianhydride were used in place of N,N-bis(3-aminophenyl)-5-hydroxyisophthalamide and 3,4,3',4'-benzophenonetetracarboxylic dianhydride, respectively, to give a polyamideimide resin having an intrinsic viscosity of 0.49 dl/g. Similar tests as in Example 11 confirmed that the resin has a repeating unit shown in Table below.

EXAMPLE 19

Substantially the same procedures as in Example 11 were repeated except that 19.5 g (50 mmol) of N,N-bis(3-amino-2-methylphenyl)-5-hydroxyisophthalamide and 15 g (50 mmol) of 4,4'-biphthalic dianhydride were used in place of N,N-bis(3-aminophenyl)-5-hydroxyisophthalamide and 3,4,3',4'-benzophenonetetracarboxylic dianhydride, respectively, to give a polyamideimide resin having an intrinsic viscosity of 0.49 dl/g. Similar tests as in Example 11 confirmed that the resin has a repeating unit shown in Table below.

EXAMPLE 20

A solution of 14.5 g (40 mmol) of N,N'-bis(3-aminophenyl)-5-hydroxyisophthalamide, 1.1 g (10 mmol) of m-phenylenediamine and 16 g (50 mmol) of 3,4,3',4'-benzophenonetetracarboxylic dianhydride in 150 ml of N-methyl-2-pyrrolidone was reacted at room temperature for 6 hours in nitrogen atmosphere to give a polyamic acid solution. The polyamic acid solution is heated at 200° C. for 2 hours to perform hydration-cyclization reaction. After cooling, the resulting polymer solution was poured in a large amount of methanol. Solids which separated out were filtered and the solids were washed and dried to give a polyamideimide having an intrinsic viscosity of 0.55 dl/g.

Similar tests as in Example 11 confirmed that the resin has a repeating unit shown in Table below.

EXAMPLE 21

A solution of 14.5 g (40 mmol) of N,N'-bis(3-aminophenyl)-5-hydroxyisophthalamide, 1.2 g (10 mmol) of hexamethylenediamine and 16 g (50 mmol) of 3,4,3',4'-benzophenonetetracarboxylic dianhydride in 150 ml of N-methyl-2-pyrrolidone was reacted at room temperature for 6 hours in nitrogen atmosphere to give a polyamic acid solution. The polyamic acid solution is heated at 200° C. for 2 hours to perform hydration-cyclization reaction. After cooling, the resulting polymer solution was poured in a large amount of methanol. Solids which separated out were filtered and the solids were washed and dried to give a polyamideimide having an intrinsic viscosity of 0.52 dl/g.

Similar tests as in Example 11 confirmed that the resin has a repeating unit shown in Table below.

EXAMPLE 22

A solution of 27.3 g (50 mmol) of N,N'-bis[4-(4-aminophenoxy)phenyl]-5-hydroxyisophthalamide and 16 g (50 mmol) of 3,4,3',4'-benzophenonetetracarboxylic dianhydride in 150 ml of N-methyl-2-pyrrolidone was reacted at room temperature for 6 hours in nitrogen atmosphere to give a polyamic acid solution. The polyamic acid solution was heated at 200° C. for 2 hours and then at 250° C. for 1 hour to perform hydration-cyclization reaction. After cooling, the resulting polymer solution was poured in a large amount of methanol. Solids which separated out were filtered and the solids were washed and dried to give a polymer having an intrinsic viscosity of 0.61 dl/g.

Infrared spectral analysis showed absorption at 3220 $cm^{-1}$ ascribable to phenolic hydroxyl group, absorptions at 1723 $cm^{-1}$ and 1777 $cm^{-1}$ ascribable to imide bonds, absorption at 1665 $cm^{-1}$ ascribable to carbonyl group in amide bonds. These results confirmed that the product is a polyamideimide having a repeating unit as shown in Table below.

EXAMPLE 23

Substantially the same procedures as in Example 22 were repeated except that 32.8 g (50 mmol) of N,N-bis[4-(4aminophenylsulfonyl)phenyl]-5-hydroxyisophthalamide was used in place of 27.3 g (50 mmol) of N,N-bis[4-(4-aminophenoxy)phenyl]-5-hydroxyisophthalamide to give a polyamideimide resin having an intrinsic viscosity of 0.59 dl/g.

Similar tests as in Example 22 confirmed that the resin has a repeating unit shown in Table below.

EXAMPLE 24

Substantially the same procedures as in Example 22 were repeated except that 32.8 g (50 mmol) of N,N-bis[4-(4aminophenylsulfonyl)phenyl]-5-hydroxyisophthalamide was used in place of 27.3 g (50 mmol) of N,N-bis[4-(4-aminophenoxy)phenyl]-5-hydroxyisophthalamide to give a polyamideimide resin having an intrinsic viscosity of 0.52 dl/g.

Similar tests as in Example 22 confirmed that the resin has a repeating unit shown in Table below.

EXAMPLE 25

Substantially the same procedures as in Example 22 were repeated except that 28.7 g (50 mmol) of N,N-bis[3-(4-aminophenoxy)-4-methylphenyl]-5-hydroxyisophthalamide was used in place of 27.3 g (50 mmol) of N,N-bis[4-(4-aminophenoxy)phenyl]-5-hydroxyisophthalamide to give a polyamideimide resin having an intrinsic viscosity of 0.56 dl/g.

Similar tests as in Example 22 confirmed that the resin has a repeating unit shown in Table below.

EXAMPLE 26

Substantially the same procedures as in Example 22 were repeated except that 11 g (50 mmol) of pyromellitic dianhydride was used in place of 16 g (50 mmol) of 3,4,3',4'-benzophenonetetracarboxylic dianhydride to give a polyamideimide resin having an intrinsic viscosity of 0.64 dl/g.

Similar tests as in Example 22 confirmed that the resin has a repeating unit shown in Table below.

EXAMPLE 27

Substantially the same procedures as in Example 22 were repeated except that 29.6 g (50 mmol) of N,N-bis[4-(4aminophenylsulfenyl)phenyl]-5-hydroxyisophthalamide and 11 g (50 mmol) of pyromellitic dianhydride were used in place of 27.3 g (50 mmol) of N,N-bis[4-(4-aminophenoxy)phenyl]-5-hydroxyisophthalamide and 16 g (50 mmol) of 3,4,3',4'-benzophenonetetracarboxylic dianhydride, respectively, to give a polyamideimide resin having an intrinsic viscosity of 0.65 dl/g.

Similar tests as in Example 22 confirmed that the resin has a repeating unit shown in Table below.

EXAMPLE 28

Substantially the same procedures as in Example 22 were repeated except that 32.8 g (50 mmol) of N,N-bis[4-(4aminophenylsulfonyl)phenyl]-5-hydroxyisophthalamide and 11 g (50 mmol) of pyromellitic dianhydride were used in place of 27.3 g (50 mmol) of N,N-bis[4-(4-aminophenoxy)phenyl]-5hydroxyisophthalamide and 16 g (50 mmol) of 3,4,3',4'- benzophenonetetracarboxylic dianhydride, respectively, to give a polyamideimide resin having an intrinsic viscosity of 0.68 dl/g.

Similar tests as in Example 22 confirmed that the resin has a repeating unit shown in Table below.

EXAMPLE 29

Substantially the same procedures as in Example 22 were repeated except that 28.7 g (50 mmol) of N,N-bis[3-(4-aminophenoxy)-4-methylphenyl]-5-hydroxyisophthalamide and 11 g (50 mmol) of pyromellitic dianhydride were used in place of 27.3 g (50 mmol) of N,N bis[4-(4-aminophenoxy)phenyl] 5-hydroxyisophthalamide and 16 (50 mmol) of 3,4,3',4'-benzophenonetetracarboxylic dianhydride, respectively, to give a polyamideimide resin having an intrinsic viscosity of 0.67 dl/g.

Similar tests as in Example 22 confirmed that the resin has a repeating unit shown in Table below.

EXAMPLE 30

Substantially the same procedures as in Example 22 were repeated except that 14.7 g (50 mmol) of 4,4'-biphthalic dianhydride was used in place of 16 g (50 mmol) of 3,4,3',4'-benzophenonetetracarboxylic dianhydride to give a polyamideimide resin having an intrinsic viscosity of 0.59 dl/g.

Similar tests as in Example 22 confirmed that the resin has a repeating unit shown in Table below.

EXAMPLE 31

Substantially the same procedures as in Example 22 were repeated except that 29.6 g (50 mmol) of N,N-bis[4-(4-aminophenylsulfenyl)phenyl]-5-hydroxyisophthalamide and 14.7 g (50 mmol) of 4,4'-biphthalic dianhydride were used in place of 27.3 g (50 mmol) of N,N-bis[4-(4-aminophenoxy)phenyl]-5-hydroxyisophthalamide and 16 g (50 mmol) of 3,4,3',4'-benzophenonetetracarboxylic dianhydride, respectively, to give a polyamideimide resin having an intrinsic viscosity of 0.55 dl/g.

Similar tests as in Example 22 confirmed that the resin has a repeating unit shown in Table below.

EXAMPLE 32

Substantially the same procedures as in Example 22 were repeated except that 32.8 g (50 mmol) of N,N'-bis[4-(4-aminophenylsulfonyl)phenyl]-5-hydroxyisophthalamide and 14.7 g (50 mmol) of 4,4'-biphthalic dianhydride were used in place of 27.3 g (50 mmol) of N,N'-bis[4-(4-aminophenoxy)phenyl]-5-hydroxyisophthalamide and 16 g (50 mmol) of 3,4,3',4'-benzophenonetetracarboxylic dianhydride, respectively, to give a polyamideimide resin having an intrinsic viscosity of 0.53 dl/g.

Similar tests as in Example 22 confirmed that the resin has a repeating unit shown in Table below.

EXAMPLE 33

Substantially the same procedures as in Example 22 were repeated except that 28.7 g (50 mmol) of N,N'-bis[3-(4-aminophenoxy)-4-methylphenyl]-5-hydroxyisophthalamide and 14.7 g (50 mmol) of 4,4'-biphthalic dianhydride were used in place of 27.3 g (50 mmol) of N,N'-bis[4-(4-aminophenoxy)phenyl]-5-hydroxyisophthalamide and 16 g (50 mmol) of 3,4,3',4'-benzophenonetetracarboxylic dianhydride, respectively, to give a polyamideimide resin having an intrinsic viscosity of 0.57 dl/g.

Similar tests as in Example 22 confirmed that the resin has a repeating unit shown in Table below.

EXAMPLE 34

A solution of 21.8 g (40 mmol) of N,N'-bis[4-(4-aminophenoxy)phenyl]-5-hydroxyisophthalamide, 1.2 g (10 mmol) of m-phenylenediamine and 16 g (50 mmol) of 3,4,3',4'-benzophenonetetracarboxylic dianhydride in 150 ml of N-methyl-2-pyrrolidone was reacted at room temperature for 6 hours in nitrogen atmosphere to give a polyamic acid solution. The polyamic acid solution was heated at 200° C. for 2 hours and then at 250° C. for 1 hour to perform hydration-cyclization reaction. After cooling, the resulting polymer solution was poured in a large amount of methanol. Solids which separated out were filtered and the solids were washed and dried to give a polymer having an intrinsic viscosity of 0.55 dl/g.

Similar tests as in Example 11 confirmed that the resin has a repeating unit shown in Table below.

EXAMPLE 35

A solution of 21.8 g (40 mmol) of N,N'-bis[4-(4aminophenoxy)phenyl]-5-hydroxyisophthalamide, 1.2 g (10 mmol) of hexamethylenediamine and 14.7 g (50 mmol) of 4,4-'4,4'-biphthalic dianhydride in 150 ml of N-methyl-2pyrrolidone was reacted at room temperature for 6 hours in nitrogen atmosphere to give a polyamic acid solution. The polyamic acid solution was heated to 200° C. for 2 hours and then at 250° C. for 1 hour to perform hydration-cyclization reaction. After cooling, the resulting polymer solution was poured in a large amount of methanol. Solids which separated out were filtered and the solids were washed and dried to give a polymer having an intrinsic viscosity of 0.53 dl/g.

Similar tests as in Example 11 confirmed that the resin has a repeating unit shown in Table below.

In the following table, symbol "Z" represents a group of formula:

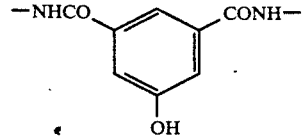

TABLE

Example 11–17: chemical structures (not transcribed as text).

TABLE-continued

| Example 18 | (structure) |
| Example 19 | (structure) |
| Example 20 | (structure) |
| Example 21 | (structure) |
| Example 22 | (structure) |
| Example 23 | (structure) |

TABLE-continued
Example 24 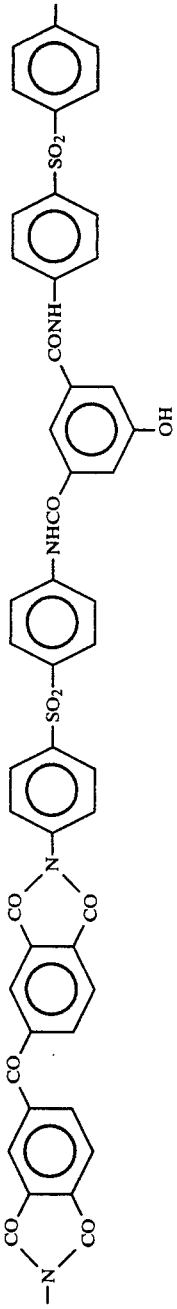
Example 25 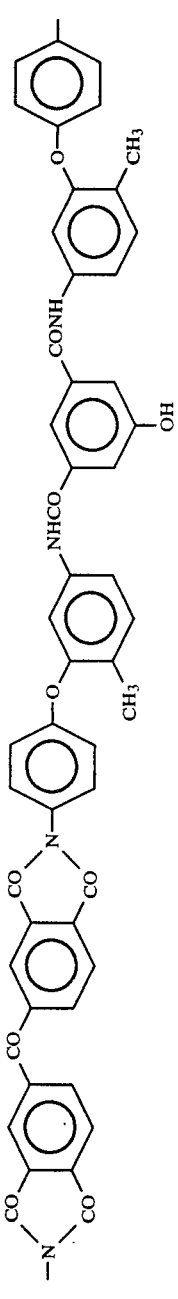
Example 26 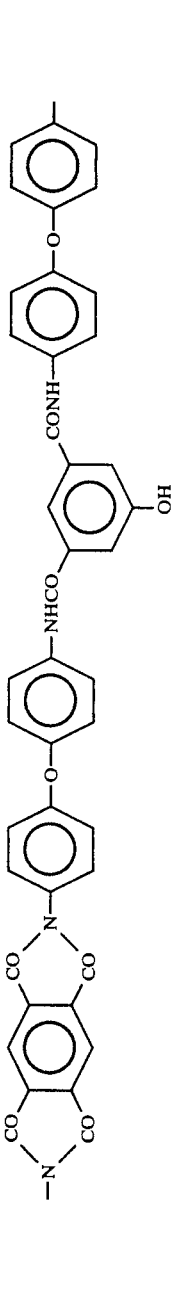
Example 27 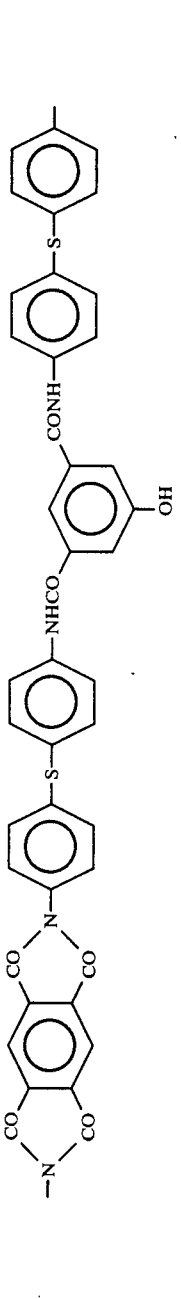
Example 28 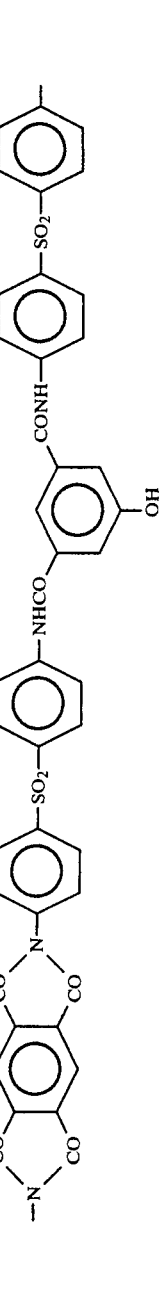

TABLE-continued

Example 29

Example 30

Example 31

Example 32

Example 33

TABLE-continued
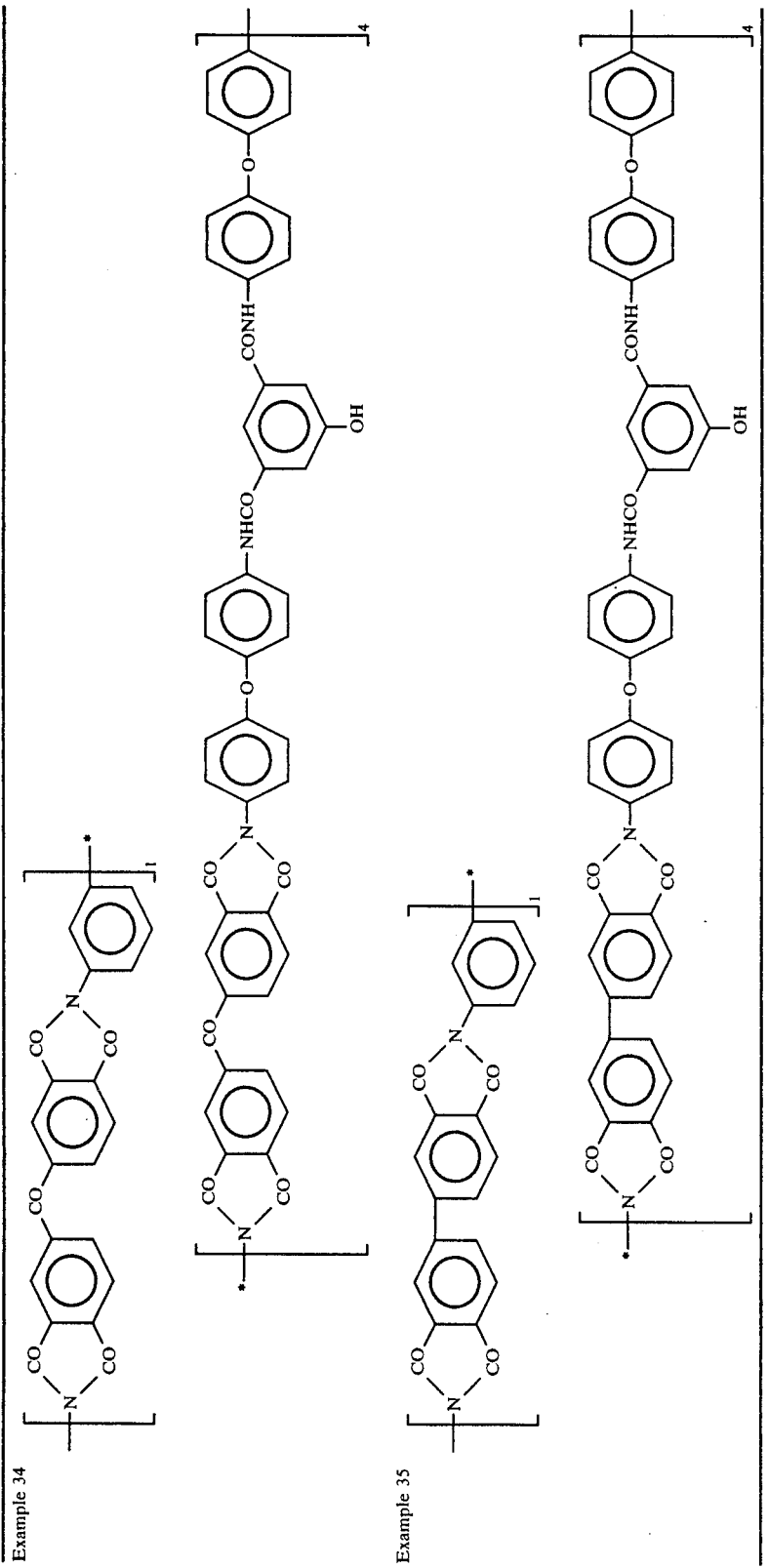
Example 34
Example 35

What is claimed is:

1. A diamine compound represented by general formula (I) below:

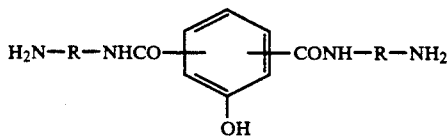  (I)

wherein R is a $C_1$-$C_{12}$ alkylene group which is unsubstituted or substituted, a group of formula (II)

  (II)

where $R^1$ and $R^2$, which are the same or different, each represents a hydrogen atom, a lower alkyl group, a halogen atom, a nitrile group, a nitro group, an alkoxy group or a hydroxyl group, or a group of formula (III)

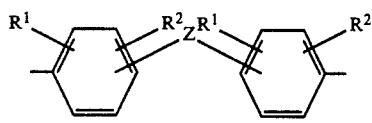  (III)

where $R^1$ and $R^2$ have the same meanings as defined above; and

Z is a simple chemical bond, —O—, >C=O, —$CH_2$—, —S—, —SO—, or —$SO_2$—.

2. A method of producing a diamine compound represented by general formula (I) below:

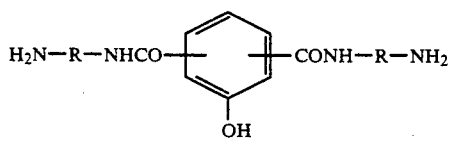  (I)

wherein R is a $C_1$-$C_{12}$ alkylene group which is unsubstituted or substituted, a group of formula (II)

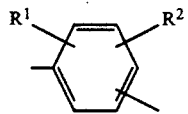  (II)

where $R^1$ and $R^2$, which are the same or different, each represents a hydrogen atom, a lower alkyl group, a halogen atom, a nitrile group, a nitro group, an alkoxy group or a hydroxyl group, or a group of formula (III)

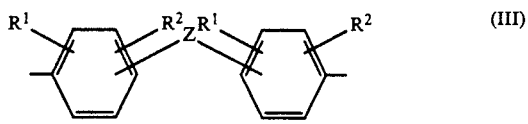  (III)

where $R^1$ and $R^2$ have the same meaning as defined above; and

Z is a simple chemical bond, —O—, >C=O, —$CH_2$—, —S—, —SO—, or —$SO_2$—, which comprises reducing a dinitro compound of general formula (IV)

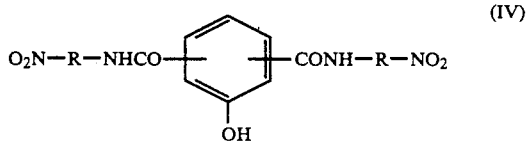  (IV)

wherein R has the same meaning as defined above.

3. A polyamideimide resin having a repeating unit represented by general formula (IV) below:

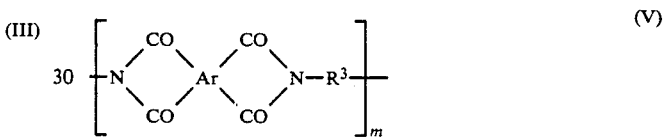  (V)

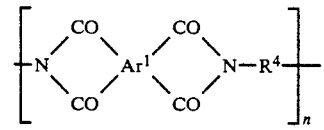

wherein Ar and $Ar^1$, which are the same or different, each represents a tetravalent aromatic residue to which two pairs of carbonyl groups are attached directly at four carbon atoms thereof, respectively, the two carbonyl groups in each one of the two pairs of carbonyl groups being attached to neighboring carbon atoms; $R^3$ is a group of general formula (VI) below:

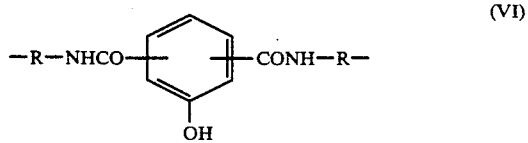  (VI)

where R has the same meaning as defined above; $R^4$ is a divalent organic residue selected from aliphatic, aromatic and alicyclic groups other than those represented by $R^3$; and m and n are each zero or a positive integer which satisfy $m \geq 2n$.

* * * * *